United States Patent [19]
Dillon et al.

[11] Patent Number: 6,165,157
[45] Date of Patent: Dec. 26, 2000

[54] NEEDLE GUARD

[75] Inventors: Jagmohanbir Singh Dillon, Bonython Act; William Leonard Mobbs, Wanniassa Act, both of Australia

[73] Assignee: Noble House Group Pty. Ltd., Australia

[21] Appl. No.: 09/161,730

[22] Filed: Sep. 29, 1998

Related U.S. Application Data

[63] Continuation-in-part of application No. 08/727,415, filed as application No. PCT/AU95/00224, Apr. 20, 1995, Pat. No. 5,833,670.

[30] Foreign Application Priority Data

Apr. 20, 1994 [AU] Australia ................................ PM5206

[51] Int. Cl.⁷ ...................................................... A61M 5/00
[52] U.S. Cl. ........................ 604/263; 604/192; 604/171; 128/919
[58] Field of Search ............................. 128/919; 604/263, 604/110, 192, 198, 170, 171, 164.01, 164.07, 164.08, 165.01, 165.02, 165.04

[56] References Cited

U.S. PATENT DOCUMENTS

| | | | |
|---|---|---|---|
| 5,192,275 | 3/1993 | Burns | 604/263 |
| 5,443,703 | 8/1995 | Utterberg et al. | 604/52 |
| 5,562,637 | 10/1996 | Utterberg | 604/263 |

FOREIGN PATENT DOCUMENTS

WO 92/04073  3/1992  WIPO ..................................... 604/263

*Primary Examiner*—Wynn Wood Coggins
*Assistant Examiner*—Deborah Blyveis
*Attorney, Agent, or Firm*—Kilpatrick Stockton LLP

[57] ABSTRACT

This invention includes protective devices for protecting against needle-stick injury by a medical catheter or needle. More particularly, the invention is concerned with guards for use with wingless needle assemblies of the type used by blood banks. However, it is also applicable to winged needle assemblies used for other medical purposes, such as the intravenous (IV) infusion of fluids. The needle or catheter assemblies of the type concerned here, comprise a needle, a needle mount or block, and a flexible tube, which are connected at one end to the needle via the needle mount and at the other end to a blood collection bag or to an IV fluid source. A winged catheter or needle assembly is one having a pair of flexible wing-like protrusions extending laterally from its mount, the wings being taped to the user's skin to keep the needle in place over the long periods of time often needed for IV infusions.

14 Claims, 5 Drawing Sheets

NEEDLE GUARD

This application is a continuation-in-part of applicant's copending application titled PROTECTIVE DEVICE having U.S. Ser. No. 08/727,415 filed Oct. 18, 1996, now U.S. Pat. No. 5,833,670, which is a national stage of PCT/AU95/00224 filed Apr. 20, 1995.

FIELD OF THE INVENTION

This invention relates to protective devices for protecting against needle-stick injury by a medical catheter or needle. More particularly, the invention is concerned with guards for use with wingless needle assemblies of the type used by blood banks. However, it is also applicable to winged needle assemblies used for other medical purposes, such as the intravenous (IV) infusion of fluids.

BACKGROUND

This invention includes protective devices for protecting against needle-stick injury by a medical catheter or needle. More particularly, the invention is concerned with guards for use with wingless needle assemblies of the type used by blood banks. However, it is also applicable to winged needle assemblies used for other medical purposes, such as the intravenous (IV) infusion of fluids. The needle or catheter assemblies of the type concerned here, comprise a needle, a needle mount or block, and a flexible tube, which are connected at one end to the needle via the needle mount and at the other end to a blood collection bag or to an IV fluid source. A winged catheter or needle assembly is one having a pair of flexible wing-like protrusions extending laterally from its mount, the wings being taped to the user's skin to keep the needle in place over the long periods of time often needed for IV infusions.

To use a wingless needle assembly for blood collection, the phlebotomist holds the needle mount with the bevel of the needle facing upwards and inserts the needle into a vein in the donor's lower arm, which is supported substantially horizontally. The tube of the assembly may then be taped to the donor's arm to hold the needle in place for the few minutes during which a unit of blood (generally 500 ml) is withdrawn. To remove the needle, the phlebotomist removes the tape, grasps the mount and withdraws the needle while pressing a swab onto the puncture site. The tube is then stripped of blood, sealed and cut so that the needle can be disposed of in a 'sharps bin'. It is during the latter actions that there is significant danger of needle-stick injury and/or contact with blood exuded from the needle ('blood-splash,' contact).

Another difficulty with this procedure is that, since the needle mount has no wings, it is readily rotated and moved by the resilience of the previously coiled tube. Even taping the tube in place often does not prevent further rotation of the needle mount. Such rotation is undesirable, as it is likely to place the bevel of the needle against the side or bottom surface of the donor's vein, thereby occluding the lumen and restricting blood flow. Rotation or longitudinal movement may also result in the point of the needle scratching or piercing the internal wall of the vein.

U.S. Pat. No. 5,376,075 to Haughton discloses a tubular needle guard that permanently houses the needle and its mount, the needle being extended from the device to allow venipuncture and then being snapped back into the device under spring action after use. The guard is provided with flexible wings by which it and the extended needle can be manipulated to effect the venipuncture. International patent application WO 92/04073 by Van den Haak also discloses a tubular needle guard that is provided with wings whereby the needle may be inserted and stabilized after insertion. Such devices require specialized needle assemblies and cannot be used with standard bloodpack needle assemblies, which have needle mounts that vary in shape according to manufacturer or model. Moreover, these prior art guards deny the phlebotomist the direct control and feel obtained when the needle mount itself is gripped to effect needle insertion in the normal way.

U.S. Pat. No. 5,112,313 to Sallee discloses a needle guard suitable for use with a wide variety of wingless needle assemblies. This guard is simply an open box that is inverted over the needle and mount after needle insertion and is secured to the patient or donor's skin by means of integral self-adhesive flaps. The guard is intended to prevent the needle mount from being inadvertently knocked after needle-insertion. It does not fit closely enough over the needle mount to restrain it against movement or rotation via the tube and does not prevent needle-stick or blood-splash after the needle is withdrawn.

SUMMARY OF THE INVENTION

Embodiment of the present invention includes protective devices for protecting against needle-stick injury by a medical catheter or needle. More particularly, the present invention is concerned with guards for use with wingless needle assemblies of the type used by blood banks. However, it is also applicable to winged needle assemblies used for other medical purposes, such as the intravenous (IV) infusion of fluids. The needle or catheter assemblies of the type concerned here, comprise a needle, a needle mount or block, and a flexible tube, which are connected at one end to the needle via the needle mount and at the other end to a blood collection bag or to an IV fluid source. A winged catheter or needle assembly is one having a pair of flexible wing-like protrusions extending laterally from its mount, the wings being taped to the user's skin to keep the needle in place over the long periods of time often needed for IV infusions.

From one aspect, the guard of the present invention comprises a hollow sleeve member adapted to be slidably mounted on the flexible tube of a winged or wingless needle assembly so that it can be positioned: (i) on the tube well clear of the needle mount in a first non-shielding position to allow the phlebotomist to grip the needle mount and insert the needle into the donor or patient in the normal manner, (ii) so that it can be moved forward to restrain relative movement of the needle mount during blood collection or infusion, and (iii), so that the needle can be withdrawn from the donor or patient directly into the guard by pulling on the tube while holding the guard on the donor or patient. Preferably, when the needle mount is pulled right into the sleeve, it is engaged by a fixing feature within the sleeve so that it cannot be moved forward again to expose the needle point.

The sleeve member preferably has a front opening adapted to loosely accommodate the needle mount and a rear opening adapted to loosely accommodate the tube. However, the rear opening is not large enough to allow the needle mount to pass therethrough. The sleeve may be injection-molded from plastics material so as to comprise two sub-members that can be hinged, clipped or otherwise fixed together about the tube of the needle assembly so as to be slidingly mounted thereon with the tube passing axially through the sleeve.

A resilient restraining feature is provided at or near the front aperture of the sleeve so that a needle mount can be partially entered into the aperture and engaged by the restraining feature. This inhibits relative rotation (and longitudinal movement) of the needle mount with respect to the sleeve of the guard during blood collection or infusion. During that time, the guard may be taped to the arm of the donor or patient to inhibit movement of the guard with respect to the donor or patient. The restraining feature also assists in maintaining the needle at a comfortable angle in the arm of the donor or patient.

The needle is more effectively restrained in this manner than by taping the tube to the donor (as in conventional practice in blood collection). The surface area provided by the exterior of the guard is much greater than that of the tube, and, the guard is preferably formed with a flat underneath surface that rests on the skin of the donor or patient. Finally, because the needle can be drawn directly into the guard as it is being withdrawn from the patient or donor by pulling on the tube, and because the puncture site and the open end of the guard are covered by a swab, the chance for needle-stick injury or blood-splash contact is minimal.

The restraining and/or the fixing features preferably comprise flexible prongs struck from the walls of the sleeve. In an embodiment of the present invention, the prongs of the restraining feature are shaped like flexible loops or rearwardly facing barbs that extend inward from the walls of the sleeve member near the distal or forward end thereof to resiliently engage a needle mount that is at least partially entered into the sleeve member. The use of loop-form prongs has the advantage that a needle block, which is prematurely pulled into the sleeve past the restraining features, can be withdrawn again if desired, whereas this may not be possible if the prongs are barblike. In another form, the restraining feature comprises one or more resilient pads located within the sleeve member near its distal end. In yet another form, the restraining feature comprises one or more inwardly extending protrusions supported by resiliently deformable portions of the sleeve. Such pads or protrusions also allow withdrawal of the needle mount. However, the flexibility and positioning of the restraining feature is preferably such that a variety of standard-form needle mounts can be accommodated and engaged when entered into the forward end of the sleeve member. When the needle mount is engaged by the restraining feature, the guard is in the aforesaid second non-shielding position relative to the needle assembly.

The fixing means preferably comprise barb-like protrusions or prongs, which extend into the sleeve member near its proximal or rear end. Such barbs are adapted to bend or otherwise deform as the needle mount is pulled past them. When the needle mount is withdrawn sufficiently to clear such barb-like protrusions, the protrusions snap back into place to effectively lock the mount in the sleeve member. The sleeve or guard is then in the third or fully-shielding position relative to the needle assembly.

Where prongs are used for the restraining and/or the fixing features, it is preferable that they be mounted in opposing pairs that extend from the top and bottom faces of the sleeve member. The prongs of the restraining and/or the fixing features are preferably arranged to lightly grip the tube of the needle assembly so that the guard does not slide down the tube under gravity and yet is readily movable in either direction when desired.

The use of opposed pairs of prongs in which the prongs of each pair are laterally spaced has the advantage that axial rotational movement of a needle mount engaged thereby is inhibited. Further, if the prongs extend from the top and bottom faces of the sleeve member, this member can easily be of a rectangular shape having a flat bottom face and a width that is greater than it is height. Such a shape strongly inhibits axial rotation under any residual torque in the tube when the guard is taped to the arm of a donor or patient.

Though the needle mount and needle can be withdrawn into the sleeve member of the guard using one hand by gripping the tube between the fingers and the palm of the hand and pressing the thumb against the rear end of the sleeve member, this tends to raise the guard from the donor's arm. It is preferable to press downwards and forwards on the top of the guard to achieve one-handed withdrawal of the needle. Preferably, this is facilitated by providing an actuator on the upper face of the sleeve member near the rear end thereof for improving the grip between the thumb and the upper face of the sleeve. The actuator may simply comprise a raised or depressed portion of the sleeve member that forms a knob or depression for the thumb of the user.

To achieve the stated and other features, advantages, and objects of the present invention, an embodiment of the invention provides a protective device for a conventional catheter assembly of the type used by blood banks and including a needle mount having a first and a second end, a needle extending from the first end of the needle mount, and a conduit extending from the second end of the needle mount, the protective device comprising: a sleeve member attachable to the catheter assembly such that in a first position, the sleeve member is slidable both toward and away from the needle mount upon the length of the conduit, and the needle block may be grasped by a user while both the needle block and the needle are fully unshielded by the sleeve member; the sleeve member being movable from the first position to a second position in which the sleeve member engages the needle mount, such that the needle mount is shielded by the sleeve member and the needle is unshielded, and wherein the needle mount is held against rotation relative to the sleeve member; and the sleeve member being movable from the second position to a third position in which the sleeve member engages the needle mount, such that the needle mount and the needle are fully shielded by the sleeve member; and wherein the sleeve includes means for restraining the sleeve member from being moved from the second position to the first position and for preventing the sleeve member from being moved from the third position to the second position.

To achieve the stated and other features, advantages, and objects of the present invention, an embodiment of the invention provides a protective device and catheter assembly, comprising: a catheter assembly of the type used by blood banks and including a needle mount having a first and a second end, a needle extending from the first end of the needle mount, and a conduit extending from the second end of the needle mount; and a protective device including a sleeve member attachable to the catheter assembly such that in a first position, the sleeve member is slidable both toward and away from the needle mount upon the length of the conduit, and the needle block may be grasped by a user while both the needle block and the needle are fully unshielded by the sleeve member; the sleeve member being movable from the first position to a second position in which the sleeve member engages the needle mount, such that the needle mount is shielded by the sleeve member and the needle is unshielded, and wherein the needle mount is held relative to the sleeve member; and the sleeve member being movable from the second position to a third position in which the sleeve member engages the needle mount, such that the needle mount and the needle are fully shielded by the sleeve member; and wherein the sleeve includes means for restraining the sleeve member from being moved from the second position to the first position and for preventing the sleeve member from being moved from the third position to the second position.

To achieve the stated and other features, advantages, and objects of the present invention, an embodiment of the invention provides a needle guard for use with medical needle assemblies in which a forwardly and axially extending needle is connected to a rearwardly and axially extending flexible trailing tube by means of an axially extending needle mount which is larger in section than both the tube and the needle, the guard comprising: an elongate sleeve member having a front and a rear end, said front end having a front aperture formed therein of sufficient size to readily allow the needle mount to pass axially therethrough, and said rear end having a rear aperture formed therein of sufficient size to readily allow the tube to pass axially therethrough but not of sufficient size as to permit the needle mount to pass therethrough; and restraining means within the sleeve member near the front aperture adapted to engage and resiliently restrain the needle mount relative to the sleeve member when it is axially entered into said front aperture; the sleeve member thereby being adapted to be slidably supported on the tube of the needle assembly with the tube passing through said front and rear apertures and with the front aperture facing the needle mount, whereby the sleeve member is movable from a first non-shielding position in which it is clear of the needle mount, to a second non-shielding position in which the needle mount is at least partially entered into the front aperture and engaged by said restraining means, and to a third shielding position in which the needle mount and the needle are fully contained within the sleeve member.

Additional objects, advantages and novel features of the invention will be set forth in part in the description that follows, and in part will become more apparent to those skilled in that upon examination of the following; these features may also be learned by practice of the invention.

DETAILED DESCRIPTION

Embodiment of the present invention includes protective devices for protecting against needle-stick injury by a medical catheter or needle. More particularly, the present invention is concerned with guards for use with wingless needle assemblies of the type used by blood banks. However, it is also applicable to winged needle assemblies used for other medical purposes, such as the intravenous (IV) infusion of fluids. The needle or catheter assemblies of the type concerned here, comprise a needle, a needle mount or block, and a flexible tube, which are connected at one end to the needle via the needle mount and at the other end to a blood collection bag or to an IV fluid source. A winged catheter or needle assembly is one having a pair of flexible wing-like protrusions extending laterally from its mount, the wings being taped to the user's skin to keep the needle in place over the long periods of time often needed for IV infusions.

The first example of a protective device formed in accordance with an embodiment of the present invention, as shown in FIGS. 1a to 1e and FIG. 2, comprises a hollow guard comprising a sleeve member 10 that is of generally rectilinear form and is molded from plastics material. Guard 10 is fitted onto the trailing tube 12 of a blood-pack needle assembly 14 so that the tube passes longitudinally and generally axially through the sleeve-like member. The needle assembly comprises, in addition to tube 12, a hollow needle 16 and a needle mount 18. The tube 12 extends rearwardly from the rear or proximal end 20 of guard 10 and is connected to a blood collection bag (not shown). The tube extends forwardly from the forward end or distal end 22 of guard 10 to terminate at the needle mount 18, through which it is placed in fluid-flow connection with needle 16. Guard 10 has upper and lower side walls 24 and 26, an opening 28 (see FIG. 2) in rear end 20 of sufficient size to accommodate tube 12 and an opening 30 in its forward end 22 of sufficient size to accommodated needle mount 18. Opening 30 is large enough to easily accept the largest needle mount of commonly available needle assemblies, while opening 28 is small enough to prevent the smallest commonly used needle mount from passing therethrough.

In an embodiment of the present invention, a first pair of resilient barb-like prongs 32 extends rearwardly and inwardly from upper wall 24 of guard 10 close to forward end 22. A similar second pair of prongs 34 (see FIGS. 1b and 1e) extends inwardly and rearwardly from lower wall 26, opposite first pair 32. Prongs 32 and 34 form the restraining feature of the guard 10. A third pair of resilient barb-like prongs 36 extend rearwardly and inwardly from upper wall 24 near the rear end 20 of guard 10, and a similar fourth pair of prongs 38 extend inwardly and rearwardly from lower wall 26 opposite third pair 36. Prongs 36 and 38 form the fixing feature of the guard 10. Since all these prongs are flexible and barb-like, they will flex to allow the needle mount 18 of a needle assembly 14 to be pulled by tube 12 rearwardly past them into the sleeve member of guard 10 but will not allow the needle mount to be pushed forwards to expose the point of needle 16 from or at front aperture 30. Preferably the prongs (36 and 38) of the fixing feature are stronger and less flexible than those (32 and 34) of the restraining feature. Also preferably, the prongs of each pair are spaced laterally from one another by a distance, which is greater than the diameter of tube 12 so that the tube can pass easily between the prongs without catching thereon.

To assist manipulation of guard 10, an actuator in the form of a thumb-knob or protrusion 40 is formed on the exterior of the upper wall 24 toward the rear end 22 of guard 10. It provides an abutment against which the thumb of the user can push in order to pull the needle 16 and needle mount 18 into the guard using only one hand (as will be described below).

In this first embodiment, guard 10 is formed as unitary sleeve member and fitted onto tube 12 before the tube is connected to the blood collection or IV bag (not shown). This may be done by forming the sleeve from separate upper and lower halves or sub-members 24 and 26 that are glued or welded permanently together along joint-line 27(see FIG. 2) around tube 12 after it has been connected to the blood or IV bag.

Figure 1A:
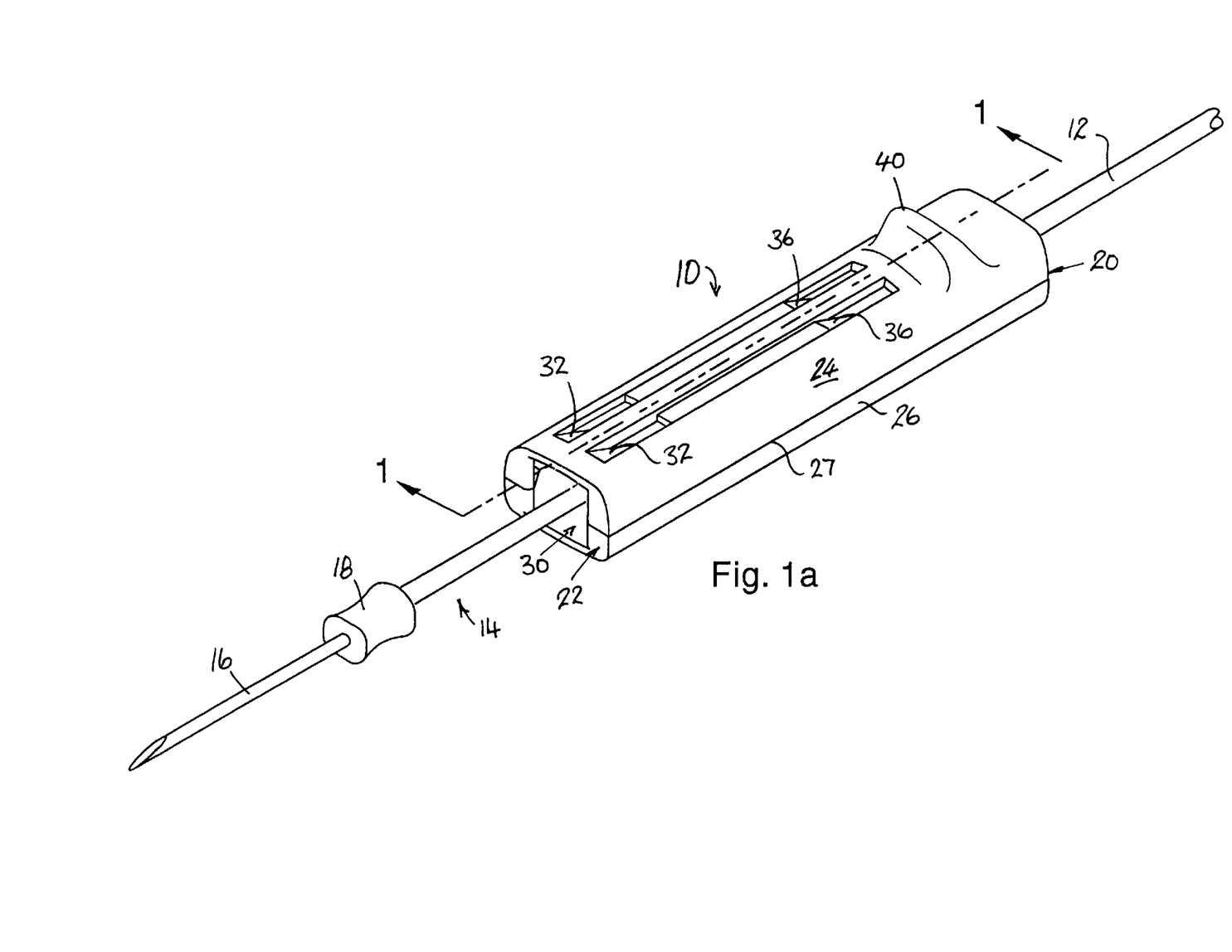
FIG. 1a is a perspective view of a standard bloodpack needle assembly fitted with a guard that forms the first embodiment of the invention, the guard being viewed from the front or distal end and being shown in the first non-shielded position relative to the needle assembly.
Figure 1B:
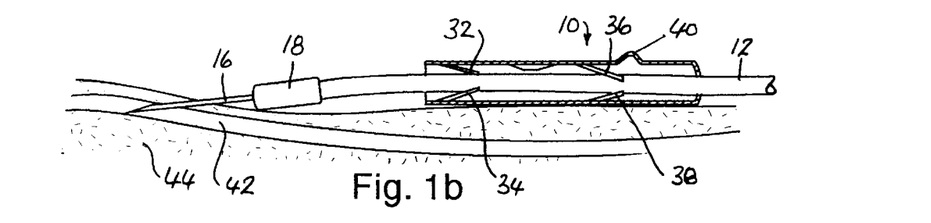
FIG. 1b is a diagrammatic sectional elevation, taken on section line 1—1 of FIG. 1a, of the guard and needle assembly of FIG. 1a, showing the needle just after insertion into the vein of a donor, the guard being in the first non-shielded position relative to the needle assembly.
Figure 1C:
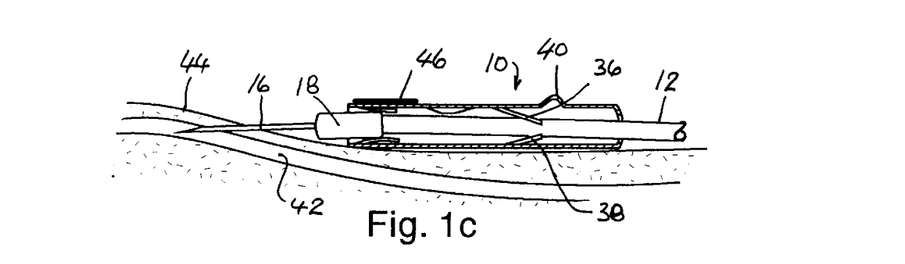
FIG. 1c is a similar view to that of FIG. 1b, showing the guard of FIG. 1a positioned to stabilize and restrain the needle mount of the needle assembly while blood is being taken, the guard being in the second nonshielding position relative to the needle assembly.

The manner of using guard 10 is illustrated in FIGS. 1b to 1e. First, with guard 10 placed clear of needle mount 18 (FIG. 1b), the mount is grasped in the usual manner by the phlebotomist (not shown) and used to insert needle 16 into the vein 42 of a donor's arm 44. Second, the phlebotomist slides guard 10 forward on tube 12 with the free hand, while still holding needle mount 18 with the other hand, until mount 18 engages the prongs 32 and 34 of the restraining feature as shown in FIG. 1c. The forward end 20 of guard 10 is then taped to the donor's arm 44 while blood is being collected, the tape being shown at 46 in FIG. 1c. Thus, the restraining feature formed by prongs 32 and 34 serves to frictionally inhibit or restrain both rotational and longitudinal movement of needle 16 relative to the donor's arm 44 during blood collection while, at the same time, holding needle 16 at a shallow angle relative to the guard for the improved comfort of the donor or patient and the rapid withdrawal of blood or infusion of liquid. This position of the guard and needle assembly is facilitated by the flexibility and opposed orientation of prongs 32 and 34, which form the restraining feature. Bottom half 26 of sleeve member 10 preferably has a flat bottom face so that, when the guard is taped to the arm of a patient or donor, it is well stabilized in the lateral direction against rolling action, should the tube 12 possess residual torque.

After sufficient blood has been collected, the phlebotomist holds the guard with one hand and removes the tape 46. She then places a swab 48 (see FIG. 1d) over the puncture site and holds it and the forward end of guard 10 against the donor's arm with the thumb 50 and first finger 52 of one hand. While holding the swab and guard immobile in this manner, the phlebotomist pulls on tube 12 with the other hand 54 to withdraw the needle from vein 42 until needle mount 18 clears prongs 32 and 34 of the restraining means. The resultant position of needle mount 18 is that shown in FIG. 1d. With needle mount 18 captured in the guard by the barb-like prongs 32 and 34, the phlebotomist can safely move the hand 54 which was pulling on the tube 12 to the position shown in FIG. 1d while swab 48 and guard 10 are kept immobile. The phlebotomist then straightens thumb 56 of hand 54 to forcefully pull needle mount 18 past prongs 36 and 38 of the fixing means. The resultant position of the needle assembly 14 relative to the needle guard 10 is shown in FIG. 1e.

With the needle 16 safely locked in the guarded position, the donor is left pressing swab 48 against the puncture site while the phlebotomist strips the tubing of blood, severs or ties tube 12 and disposes of guard 10 and needle assembly 14 without fear of needle-stick injury. Protection from blood-splash hazard may be further improved by providing a hydrophilic lining, or pad of adsorbent material, on the inside of the forward end 22 of the sleeve member 10 in the region of the point of needle. The lining can be simply provided by roughening the inside surface of the sleeve as can be obtained by the use of spark or acid treatment of the mold from which the sleeve is formed. In addition, the swab 48 may be pressed into opening 30 in forward end 22 of guard 10 before it is discarded. Because the needle is fully shielded, it does not need to be discarded into a sharps-bin.

Figure 1D:
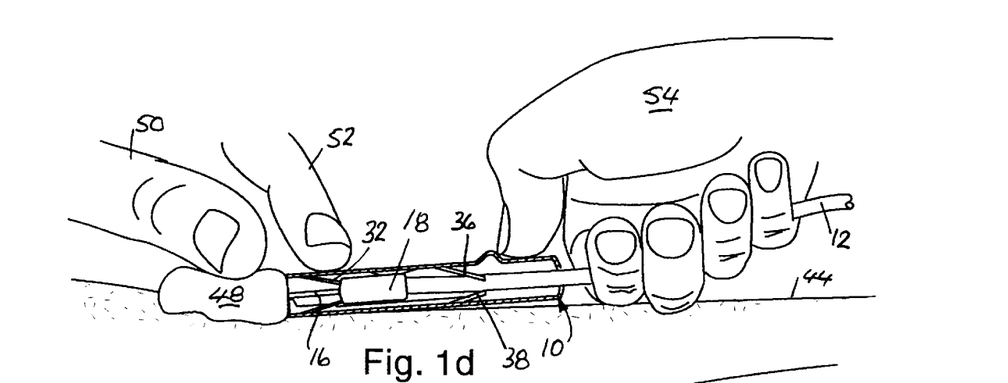
FIG. 1d is a similar view to that of FIGS. 1band 1c, showing the needle assembly partially withdrawn into the guard after termination of blood collection.
Figure 1E:
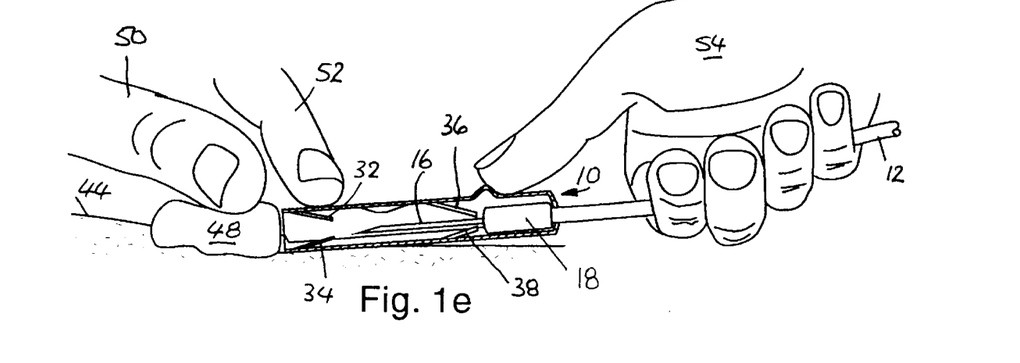
FIG. 1e is a similar view to that of FIG. 1d, showing the needle assembly fully withdrawn into the guard after termination of blood collection.
Figure 2:
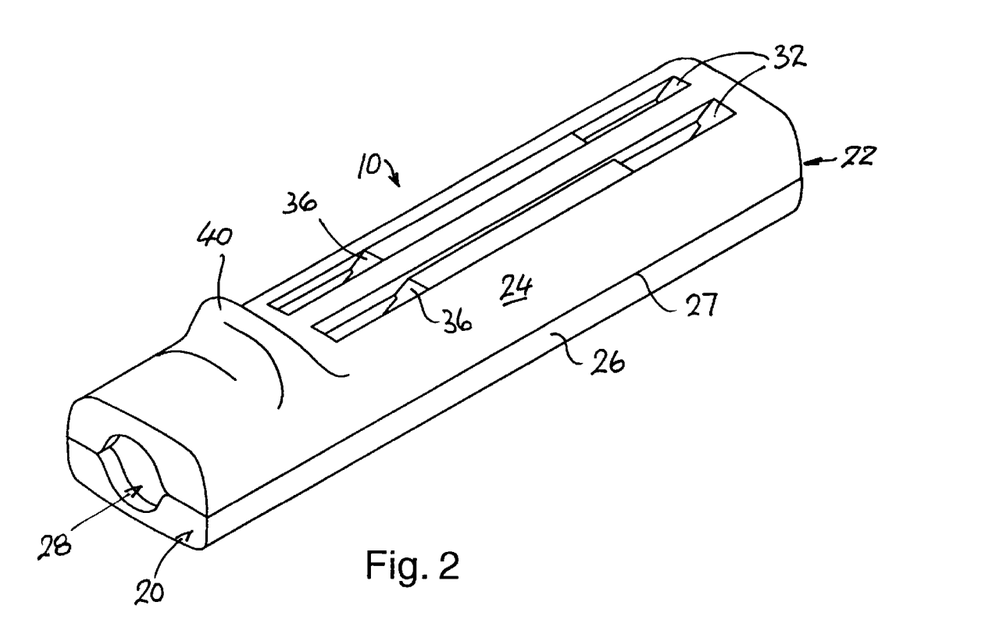
FIG. 2 is a perspective view of the guard of the first example viewed from the rear or proximal end without the needle assembly in place.

Depending on the length of the needle employed and the proportions of the restraining feature, it may be possible to move the needle mount into the position shown in FIG. 1d without discomfort to the donor while blood is being withdrawn. In this position, the prongs 32 and 34 of the restraining means prevent the needle mount from moving forwards out of the guard, providing an added level of safety.

Figure 5:
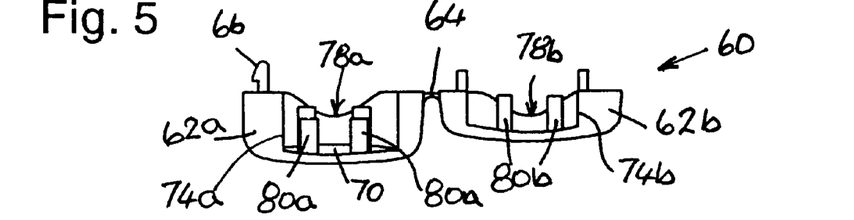
FIG. 5 is an end view, taken on plane 5—5 of FIG. 4 of the guard of FIG. 4.
Figure 6:
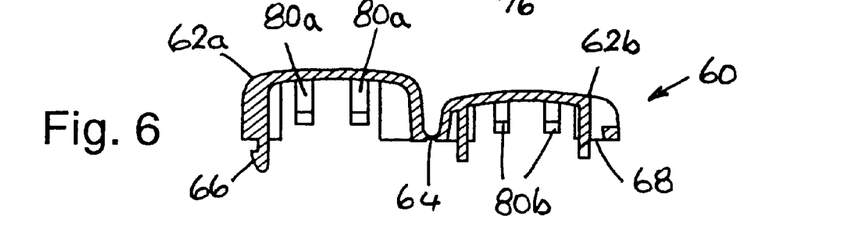
FIG. 6 is a sectional elevation of the guard of FIG. 4 taken on plane 6—6 of FIG. 4.

The second embodiment of the invention, illustrated in FIGS. 3 to 6 includes a guard 60, which comprises an upper longitudinal shell-like sub-member 62a and a similar lower sub-member 62b joined along one of their edges by an integral hinge 64 (see FIG. 5). Hinge 64 allows sub-members 62a and 62b to be closed around the tube of a needle assembly (not shown). Three hook-shaped spigots 66 (see FIG. 5) are formed on the free edge of one sub-member 62a to enter corresponding apertures 68 formed on the free edge of the other sub-member 62b so as to lock the sub-members together, after they have been folded together. Instead of a thumb-knob (40, FIG. 2) on the upper rear portion of the guard (as in the first example), the actuator of this example comprises a recessed thumb-pad 70. Apart from the fold and lock together function and the use of a thumb pad rather than a thumb knob, the guard 60 is essentially identical to guard 10 of the first example.

Figure 3:
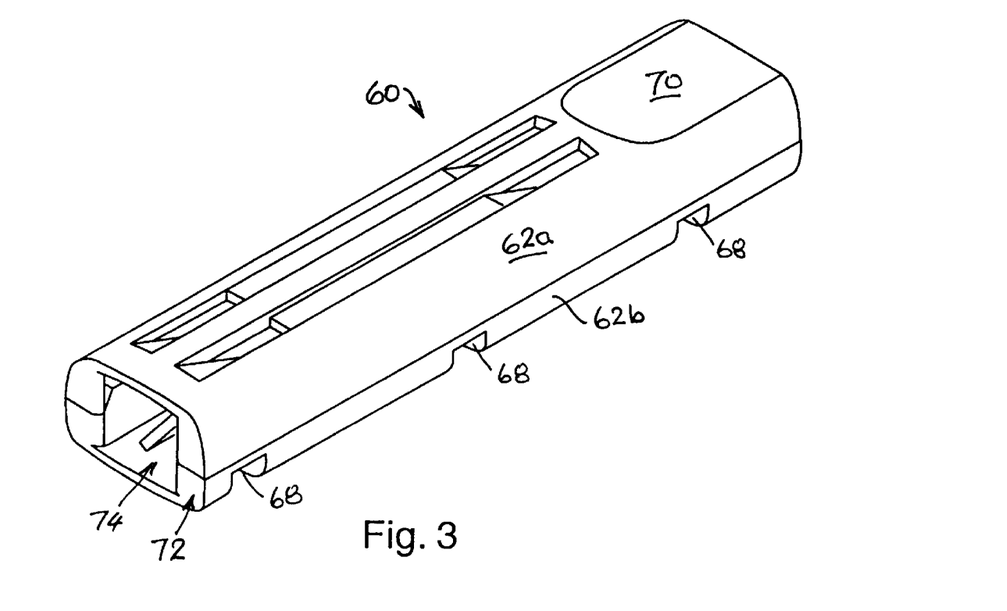
FIG. 3 is a perspective view of the guard of the second example, after it has been folded and clipped together.
Figure 4:
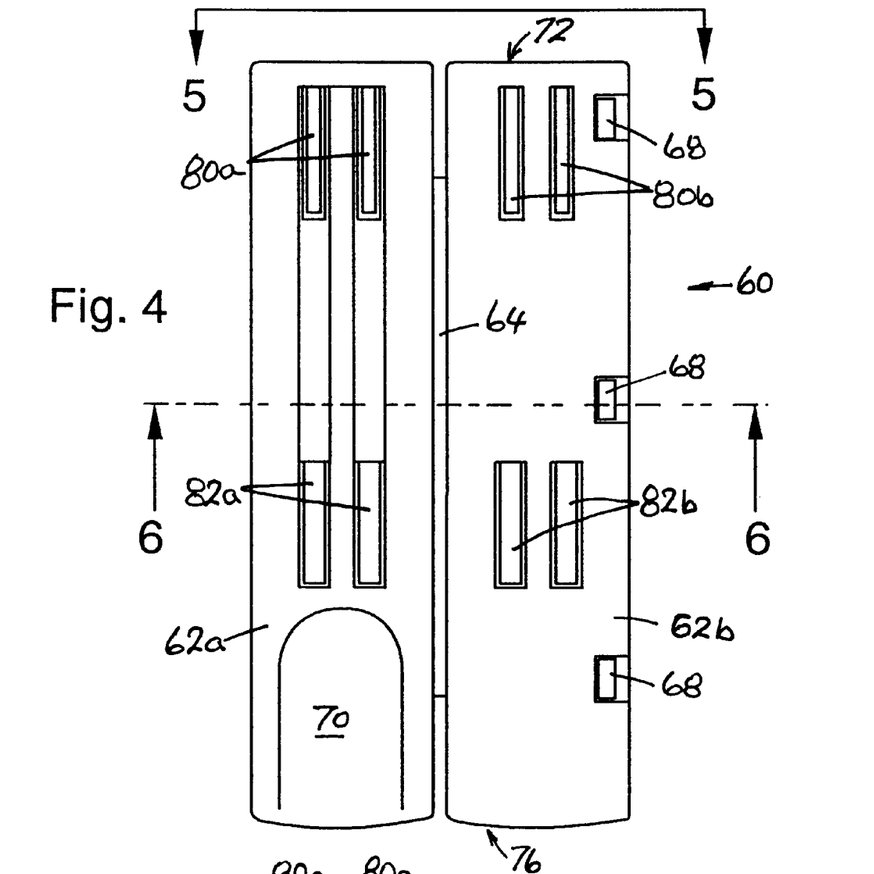
FIG. 4 is a plan view of the exterior of the guard of FIG. 3 with its sub-members arranged flat and not folded together.

In FIG. 3, guard 60 is viewed from its forward end 72 in which a rectangular opening 74 is formed to accommodate the needle mount of a needle assembly (not shown in this Figure), opening 74 being formed when semi-rectangular cutouts 74a and 74b (see FIG. 5) in the forward ends of upper and lower sub-members 62a and 62b are brought together. Similarly, a circular opening (not visible in FIG. 3, but of the same shape as opening 28 of guard 10 shown in FIG. 2) is formed in the rear or proximal end 76 (see FIG. 4) of guard 60 when corresponding semi-circular cut-outs 78a and 78b in the rear ends of sub-members 62a and 62b are brought together.

As in the first example, the restraining feature of this example are formed by two opposing pairs of comparatively slender and flexible barb-like prongs 80a and 80b that extend inwardly and rearwardly from the inside surfaces of upper and lower sub-members 62a and 62b (respectively) near the forward end 72 of guard 60. The fixing feature is formed by two similar pairs of comparatively thick and stiff prongs 82a and 82b that extend inwardly and rearwardly from the inside surfaces of sub-members 62a and 62b near the rear end 76 of the guard 60.

Guard 60 of the second example may be used in exactly the same manner as described with respect to the guard 10 of the first example, except that it is adapted to be fitted over the tube of a needle assembly just prior to use, rather than attached by the manufacturer of the blood pack.

While the guards of the first and second examples are suited for use with wingless needle assemblies, they can be modified for use with winged needle assemblies by the provision of a slot that extends from their front ends rearwards for most of the length of the guard, leaving only a small portion of the rear end of the guard joined together. Thus, in guard 60 of the second example, integral hinge need only extend a small distance from the rear end 76 of device 60, the two sub-members then being held together by one or two spigots 66 and holes 68 (see FIG. 4) arranged at the rear of the guard 60.

Figure 7:
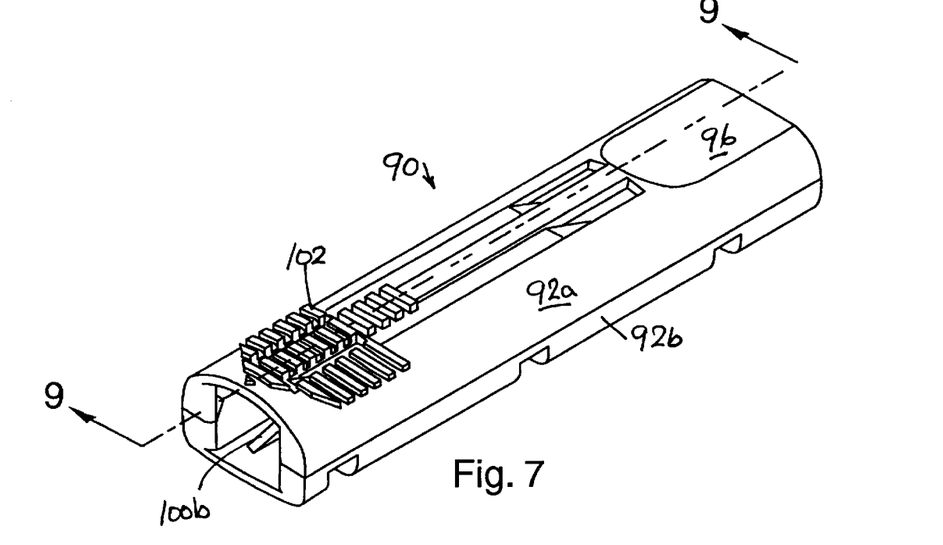
FIG. 7 is a perspective view of a guard, which comprises the third example of the present invention.
Figure 8:
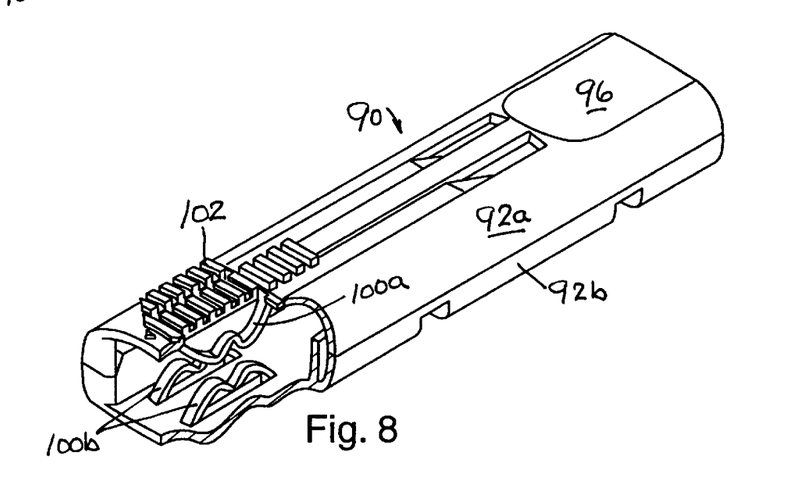
FIG. 8 is a perspective view—with portion cut-away -of the guard of FIG. 7.
Figure 9:
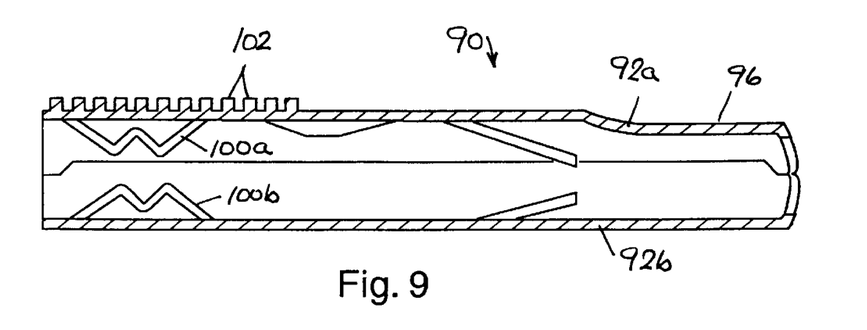
FIG. 9 is a longitudinal sectional elevation of the guard of FIG. 7, taken on the section line 9—9 of FIG. 7.

FIGS. 7 to 9 illustrate a third example of a protective device formed in accordance with the present invention. The device comprises a needle guard 90, which is similar in most respects to guard 60 of the second example, having upper and lower sub-members 92a and 92b that fold and snap together about the tube of a needle assembly (not shown). As before, the actuator comprises a thumb pad 96 on the rear end of upper member 92a and the fixing feature comprises pairs of rearwardly projecting barb-like prongs 98a and 98b, which protrude inwardly from the upper and lower sub-members 92a and 92b respectively. However, in this example, the restraining feature comprises pairs of M-shape prongs 100a and 100b which protrude into the interior of the guard from the upper and lower sub-members 92a and 92b respectively. In addition, upper sub-member 92a has a series of ribs 102 formed on the exterior of its forward or distal end. These ribs (102) form a non-slip area for the phlebotomist's fingers during the withdrawal of the needle (as in FIGS. 1d and 1e).

The use of M-shape prongs 100a and 100b, rather than the barb-like prongs of the restraining feature of the previous examples, allows the needle mount to be withdrawn from the guard should it be inadvertently pulled past them. The rear barb-like prongs 98a and 98b are such that, while it is more difficult to pull the needle mount past them, once that has been done, it will be impossible to push the needle mount forwards again using the tube of the needle assembly. The flexibility of prongs 100a and 100b may be increased, if desired, by splitting each prong in the center.

Embodiments of the present invention have now been described in fulfillment of the above objects. It will be appreciated that these examples are merely illustrative of the invention. Many variations and modifications will be apparent to those skilled in the art.

We claim:

1. A needle guard for use with a needle assembly including a needle mount having a first and a second end, a needle extending from the first end of the needle mount and a flexible trailing tube extending from the second end of the needle mount, the guard comprising:

a sleeve member adapted for slidable mounting on the trailing tube of a needle assembly for movement both toward and away from the needle mount of the assembly whereby the sleeve member can be located in a first position in which said member is clear of the needle mount so that the needle mount can be grasped by a user while both the needle mount and the needle are fully unshielded by the sleeve member; the sleeve member being slidable along the trailing tube from said first position to a second position in which the sleeve member engages the needle mount, such that in said second position the needle mount is at least partially shielded by the sleeve member, the needle is unshielded by the sleeve member and the needle mount is held against rotation relative to the sleeve member; and the sleeve member being movable from said second position to a third position in which the sleeve member engages the needle mount, such that in said third position the needle mount and the needle are fully shielded by the sleeve member; and wherein the sleeve member includes means for restraining the sleeve member from being moved from the second position to the first position and for preventing the sleeve member from being moved from the third position to the second position.

2. In combination:

a needle assembly including a needle mount having a first and a second end, a needle extending from the first end of said needle mount and a flexible trailing tube extending from the second end of the needle mount, and a needle guard comprising a sleeve member slidably mounted on the trailing tube of the needle assembly for movement both toward and away from the needle mount of the assembly whereby the sleeve member can be located in a first position in which said member is clear of the needle mount so that the needle mount can be grasped by a user while both the needle mount and the needle are fully unshielded by the sleeve member; the sleeve member being slidable along the trailing tube from said first position to a second position in which the sleeve member engages the needle mount, such that in said second position the needle mount is at least partially shielded by the sleeve member, the needle is unshielded by the sleeve member and the needle mount is held against rotation relative to the sleeve member; and the sleeve member being movable from said second position to a third position in which the sleeve member engages the needle mount, such that in said third position the needle mount and the needle are fully shielded by the sleeve member; and wherein the sleeve member includes means for restraining the sleeve member from being moved from the second position to the first position and for preventing the sleeve member from being moved from the third position to the second position.

3. A needle guard for use with medical needle assemblies in which a forwardly and axially extending needle is connected to a rearwardly and axially extending flexible trailing tube by means of an axially extending needle mount which is larger in section than both the tube and the needle, the guard comprising:

an elongate sleeve member having a front and a rear end, said front end having a front aperture formed therein of sufficient size to readily allow the needle mount to pass axially therethrough, and said rear end having a rear aperture formed therein of sufficient size to readily allow the tube to pass axially therethrough but not of sufficient size as to permit the needle mount to pass therethrough; and restraining means within the sleeve member near the front aperture adapted to engage and resiliently restrain the needle mount relative to the sleeve member when it is axially entered into said front aperture;

the sleeve member thereby being adapted to be slidably supported on the tube of the needle assembly with the tube passing through said front and rear apertures and with the front aperture facing the needle mount, whereby the sleeve member is movable from a first non-shielding position in which it is clear of the needle mount, to a second non-shielding position in which the needle mount is at least partially entered into the front aperture and engaged by said restraining means, and to a third shielding position in which the needle mount and the needle are fully contained within the sleeve member.

4. A needle guard according to claim 3, wherein the sleeve member has a peripheral wall;

wherein the restraining means comprises at least one pair of prongs extending inwards from said wall to resiliently engage the needle mount of a needle assembly which is entered into said front aperture; and the prongs of said pair of prongs are laterally spaced from one another so that, when the needle mount of a needle assembly is engaged thereby, axial rotation of the mount relative to the sleeve member is restrained.

5. A guard according to claim 4, wherein at least some of said prongs are barb-like, comprising inwardly and rearwardly extending strips adapted to flex to permit the needle mount of a needle assembly to move rearwardly therepassed but to spring back after the needle mount has so passed to inhibit the needle mount from being moved forwards again.

6. A guard according to claim 4, wherein at least some of said prongs are adapted to contact the tube of a needle assembly arranged axially within the sleeve member so as to frictionally prevent the sleeve member from sliding on the tube under gravity while not preventing the sleeve member from being readily slid along the tube by hand.

7. A guard according to claim 4, wherein each of said prongs is in the form of a loop of flexible material that extends into the sleeve member to resiliently engage the needle mount when the sleeve member is in the second non-shielding position, whereby a needle mount of a needle assembly contained within the sleeve member behind the restraining means is removable forwards from the sleeve member by deflection of said loop-form prongs.

8. A guard according to claim 3 wherein the sleeve member has a top wall and an opposing bottom wall, each wall extending from end to end of the sleeve member;

said bottom wall is substantially flat so that it is adapted to sit flat on the arm of a donor or patient;

wherein said restraining means comprises:
    a first pair of resilient prongs extending inwardly from said top wall near the forward end of the sleeve member; and
    a second pair of resilient prongs extending inwardly from said bottom wall arranged opposite said first pair of prongs; and
wherein the prongs of each of said pairs of prongs are laterally spaced from one another so that, when the needle mount of a needle assembly is engaged thereby, axial rotation of the mount relative to the sleeve member is restrained.

9. A needle guard according to claim 8, wherein said top wall and said bottom wall are joined together about a longitudinally extending integral hinge so that the top and bottom walls are hingedly closable about the tube of a needle assembly to form the sleeve member on the tube; and wherein locking means are provided for locking the top and bottom walls together after they have been brought together about the tube.

10. A guard as defined in claim 3, further including:

fixing means within the sleeve member adapted to permit the needle mount to pass within the sleeve member rearwardly to the rear end of the sleeve member and adapted to prevent the needle mount from moving forwards again, thereby capturing the needle mount between said fixing means and the rear end of the sleeve member when the sleeve member is in said third shielding position.

11. A guard according to claim 10 wherein the sleeve member has a peripheral wall;

wherein said fixing means comprises at least one pair of resilient barb-like prongs extending inwardly and rearwardly from said wall; and wherein said prongs are adapted to flex to allow the needle mount of a needle assembly to be pulled there-past when the sleeve member is moved from said second non-shielding position to said third shielding position, and to then unflex to prevent the needle mount from moving forwards relative to the sleeve member, thereby capturing the needle mount within the rear end of the sleeve member when the sleeve member is in the third shielding position.

12. A guard according to claim 11 wherein at least some of said prongs are adapted to contact the tube of a needle assembly arranged axially within the sleeve member so as to frictionally prevent the sleeve member from sliding on the tube under gravity while not preventing the sleeve member from being readily slid along the tube by hand.

13. A guard according to claim 3 wherein the sleeve member has an upper wall that extends to the rear end of the sleeve member; and wherein actuator means is formed on said wall toward the rear end of the sleeve member.

14. A guard according to claim 13 wherein said actuator means is adapted for engagement with a thumb of a user so that the sleeve member is movable from the second non-shielding position to the third shielding position by gripping the tube close to the rear end of the sleeve member in one hand, engaging said actuator means with the end of the thumb when bent and extending the thumb to force the sleeve member forwards along the tube of the needle assembly.

* * * * *